US007022117B1

(12) United States Patent
Hohla et al.

(10) Patent No.: US 7,022,117 B1
(45) Date of Patent: Apr. 4, 2006

(54) CUSTOMIZED REFRACTIVE CORRECTION

(75) Inventors: Kristian Hohla, Vaterstetten (DE);
Gerhard Youssefi, Landshut (DE);
Roland Toennies, Olching (DE)

(73) Assignee: Bausch & Lomb Incorporated,
Rochester, NY (US)

( * ) Notice: Subject to any disclaimer, the term of this patent is extended or adjusted under 35 U.S.C. 154(b) by 252 days.

(21) Appl. No.: 10/110,894

(22) PCT Filed: Oct. 20, 2000

(86) PCT No.: PCT/EP00/10379

§ 371 (c)(1),
(2), (4) Date: Sep. 30, 2002

(87) PCT Pub. No.: WO01/28478

PCT Pub. Date: Apr. 26, 2001

(30) Foreign Application Priority Data

Oct. 21, 1999  (DE) ................................ 199 50 788
Mar. 23, 2000  (DE) ................................ 100 14 482

(51) Int. Cl.
*A61F 9/008* (2006.01)
(52) U.S. Cl. ................................ 606/10; 606/5; 606/13
(58) Field of Classification Search .................... 606/5, 606/10–14; 351/212
See application file for complete search history.

(56) References Cited

U.S. PATENT DOCUMENTS

| | | | | |
|---|---|---|---|---|
| 3,689,894 A | * | 9/1972 | Laura et al. .................... | 360/55 |
| 4,988,348 A | * | 1/1991 | Bille .............................. | 606/5 |
| 5,061,342 A | * | 10/1991 | Jones ............................ | 216/26 |
| 5,312,320 A | * | 5/1994 | L'Esperance, Jr. ............. | 606/5 |
| 5,376,086 A | | 12/1994 | Khoobehi et al. | |
| 5,571,107 A | * | 11/1996 | Shaibani et al. ................ | 606/4 |
| 5,777,719 A | * | 7/1998 | Williams et al. ............. | 351/212 |
| 6,106,513 A | * | 8/2000 | McMillen et al. .............. | 606/4 |
| 6,287,296 B1 | * | 9/2001 | Seiler et al. .................... | 606/5 |

FOREIGN PATENT DOCUMENTS

| | | |
|---|---|---|
| EP | 0 257 836 | 3/1988 |
| EP | 0 280 414 | 8/1988 |
| EP | 0 619 992 | 10/1994 |
| EP | 0 714 646 | 11/1995 |
| WO | WO 93/25166 | 12/1993 |
| WO | WO 94/25107 | 4/1994 |
| WO | WO 96/21407 | 12/1995 |

* cited by examiner

*Primary Examiner*—David M. Shay (57) ABSTRACT

An aperture card is provided for insertion into a laser refractive ablation system for use in laser ablating the cornea. The aperture card is designed for single surgical use for surgical precautionary considerations and to achieve the highest quality ablations, in addition to reproducibility. The aperture card is loaded into the laser refractive ablation system in a path between the laser system and the eye. The aperture card is precisely located by positioning means and ablative lasing action is inhibited if the card is not positioned within tolerance. Alternatively, the laser system can determine the position of the aperture card and adjust a computed ablation profile or otherwise adjust the optical system to adapt for any misalignment of the apertures in the aperture card. The card contains a "soft spot" aperture capable of shaping a spatial intensity distribution with a unique profile. The profile has a substantially flat top while the sides of the profile slope until an ablation intensity threshold is reached, at which point the sides become substantially vertical. The card can contain more than one soft spot aperture along with a "hard spot" aperture that creates a square-shaped profile used for testing fluence. Each soft spot aperture is formed by a central aperture and a plurality of holes of different sizes surrounding the central aperture and arranged such that the overall diffractive effect produces a soft spot spatial intensity profile compared to the hard, square-sided profile.

43 Claims, 11 Drawing Sheets

CUSTOMIZED REFRACTIVE CORRECTION

TECHNICAL FIELD

The invention relates to refractive laser ablation systems, and, more particularly, an excimer laser refractive ablation system employing an aperture card that passes a unique ablation profile.

BACKGROUND ART

Systems for reprofiling the eye for refractive correction have become extremely popular. Such systems typically employ a 193-nanometer (nm) argon-fluoride excimer laser, passing the light to the corneal tissue, where a very precise amount of tissue is "ablated" from the eye with a laser shot. A variety of delivery mechanisms are commercially used, including systems in which a fixed spot size is moved over the surface of the eye, in which the spot size is varied, and in which erodible masks are placed in the path of the excimer laser beam. In all of these systems, the ultimate goal is to change the profile of the corneal surface by volumetrically altering the amount of tissue within the cornea. Further, these techniques have been employed on the surface of the cornea underneath the epithelia using a technique for photorefractive keratectomy (PRK) as well as the intra-cornea technique known as LASIK, or laser in situ keratomileusis.

U.S. Pat. No. 5,376,086, issued to Khoobehi et al., discloses a laser surgical method of sculpting a patient's cornea that uses a mask system with multiple openings in which laser power transmission is controlled through the use of diffraction and absorption. Each hole in the mask acts like an individual light source, distributing laser power as a function of the hole's size, shape, and overlaid coatings. By summing the power output of each hole pattern over a given area, an average power distribution is generated. The technique, however, is limited because the power transmission of the mask is tailored only to a particular corneal surface by using topographical information of that surface. The corneal surface topographic data is the controlling mechanism for constructing the pattern of the mask itself. The surgeon can observe the topographic information and then pattern the mask according to that topographic information.

The present invention is directed to improving laser ablation of eye tissue that avoids or reduces shortcomings of previous methods.

SUMMARY OF THE INVENTION

According to certain features of the invention, a laser refractive ablation system for the eye, such as a 193 nm excimer laser system, is implemented to pass a unique "truncated" intensity ablation profile, for example, a non-Gaussian profile or a truncated-Gaussian profile referred to herein as a "soft spot" profile. The "top" of the soft spot profile is substantially flattened whereas the sides of the profile slope until an ablation intensity threshold is reached, at which point the edge or sides become nearly vertical. The profile is provided using an aperture card prepared based on diffractive effects. The aperture card preferably includes 1 and 2 millimeter (mm) apertures surrounded by a plurality of extremely small holes referred to herein as "soft spot" apertures that allow the diffractive effect of the laser light to accumulate to form the desired profile. Further, the aperture card includes a "square-sided" profile aperture (referred to herein as a "hard spot" aperture) for testing the fluence of the excimer laser system.

The aperture card is intended for a single surgical use because it can exhibit changes in characteristics over time, although in some embodiments, this is not necessarily true. The card is preferably loaded for single use into the system from an aperture card holder, and transported into place using a horizontal and vertical movement robot mechanism. Then, a laser system determines whether the aperture card is properly positioned, inhibiting lasing action if the card is not positioned within tolerance. Alternatively, the laser system can determine the position and adjust the computed ablation profile or otherwise adjust the optical system to adapt for the misalignment of the aperture within the aperture card.

MODE(S) FOR CARRYING OUT THE INVENTION

Figure 1:
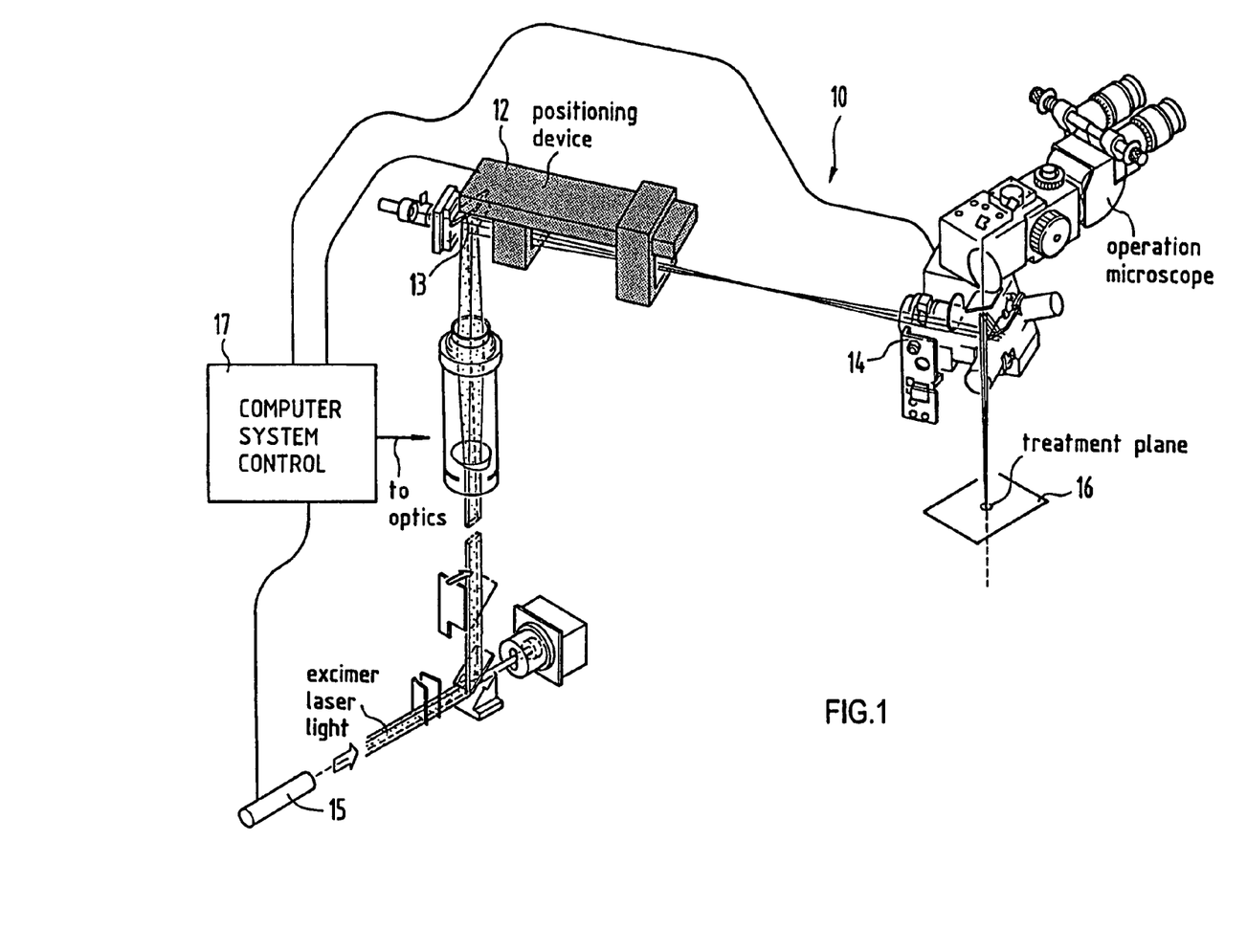
FIG. 1 illustrates a laser refractive ablation system for the eye in accordance with an embodiment of the invention.

Turning to FIG. 1, an exemplary excimer laser system 10 is illustrated in which a unique profile and aperture card handling or conveying system 12 (also referred to as a linear translation module) is shown in accordance with an embodiment of the invention. The system 12 takes the place of an iris diaphragm for beam dimensioning. It is mounted in a frame between a bending mirror 13 and a scanner block 14 (see FIG. 1). Specifically, the excimer laser system is a typical 193 nm excimer laser system. It includes an excimer laser 15 and operates as a scanning laser system employing mirrors (e.g., galvanometer driven high precision mirrors for 193 nm) to scan the laser beam to appropriate points on the cornea in a treatment plane 16. Preferably, the laser system 10 employs an eye tracking system with a tracking speed of at least 100 Hz. The laser system 10 is controlled by a control system 17, for example, a computer. The control system either can compute locally a shot pattern to achieve a desired ablation profile, or can receive an ablation profile remotely, such as according to U.S. Pat. No. 5,891,132 entitled "Distributed Excimer Laser Surgery System," and issued to Hohla. Such systems will be understood by those skilled in the art. Further, other lasers than excimer lasers may be used.

Figure 2:
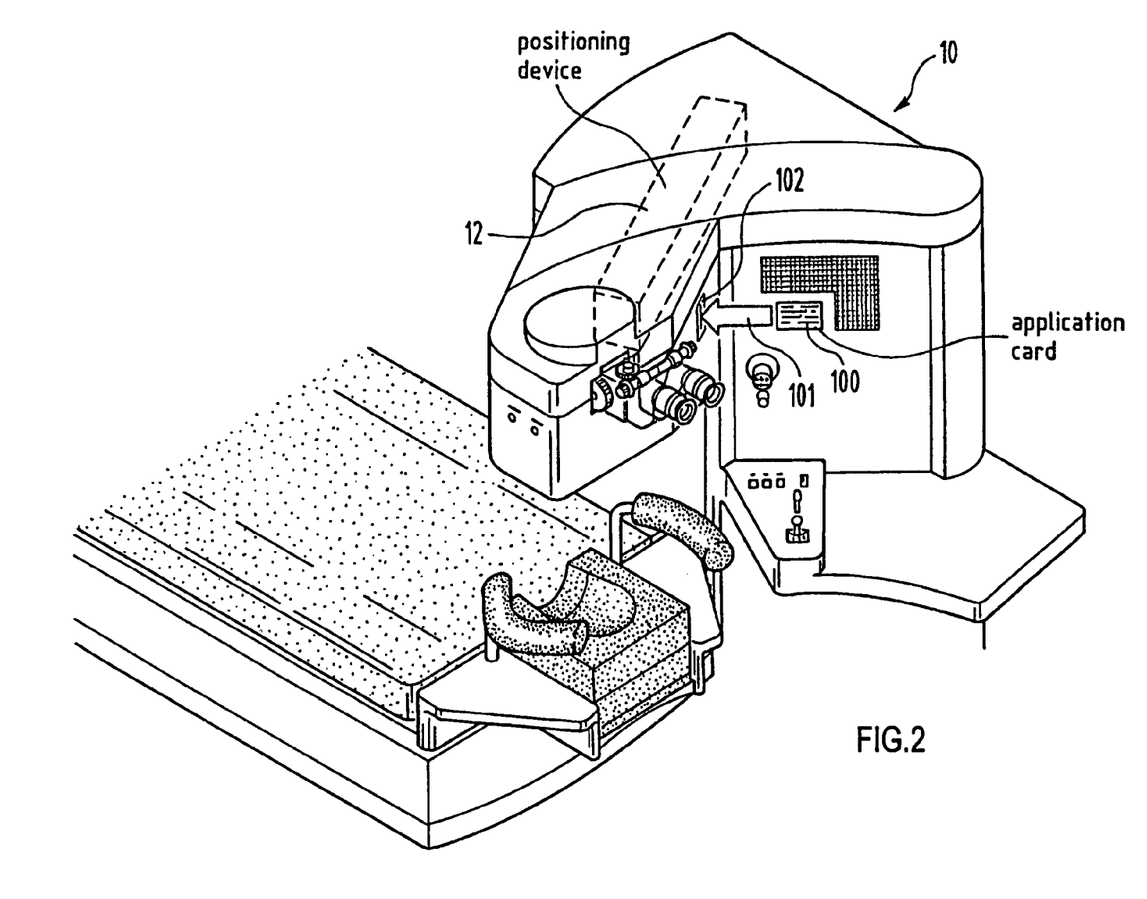
FIG. 2 illustrates the laser system of FIG. 1 that includes an aperture card in accordance with an embodiment of the invention.

In any case, according to one aspect in the invention, the system is implemented to receive an aperture card or application card 100 as shown in FIG. 2. The card 100 is precisely positioned within the laser path of the excimer laser system to pass light through apertures forming part of the aperture card. In one embodiment, the aperture card is a mask holder similar to a card-based system for chip card designs that includes a set of several high precision drillings used as reference points to the geometrical assembly of the card. The accuracy of these devices is typically down to less than 30 microns on both axes, and manufacturing processes can be automated and checked by microscopic measuring tools. In an alternative embodiment the aperture card is positioned and aligned via pressure points and fixation points in conjunction with precision machining and manufacturing. This produces single use card positioning with a repeatable accuracy in the order of 5 µm or better.

Figure 3:
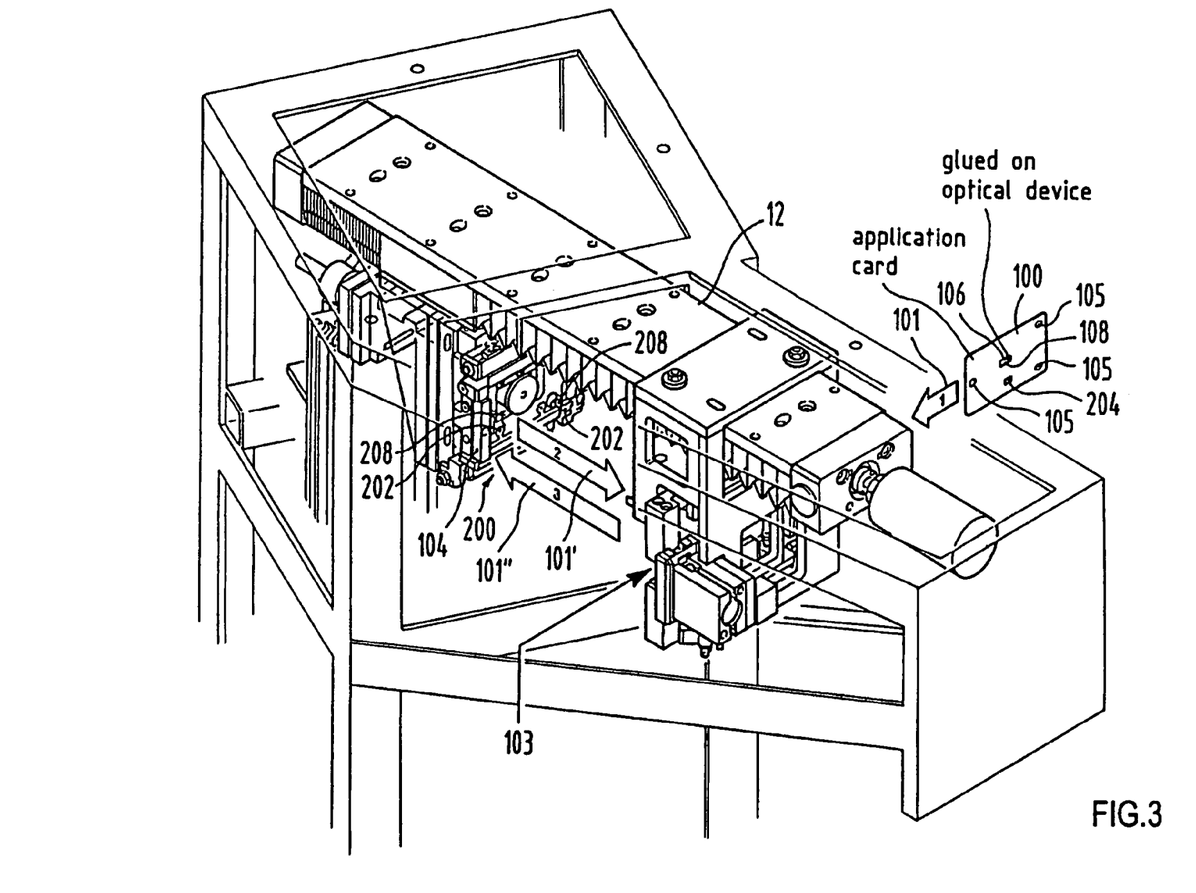
FIG. 3 illustrates a mechanism for holding an aperture card in place in accordance with an embodiment of the invention.
Figure 4:
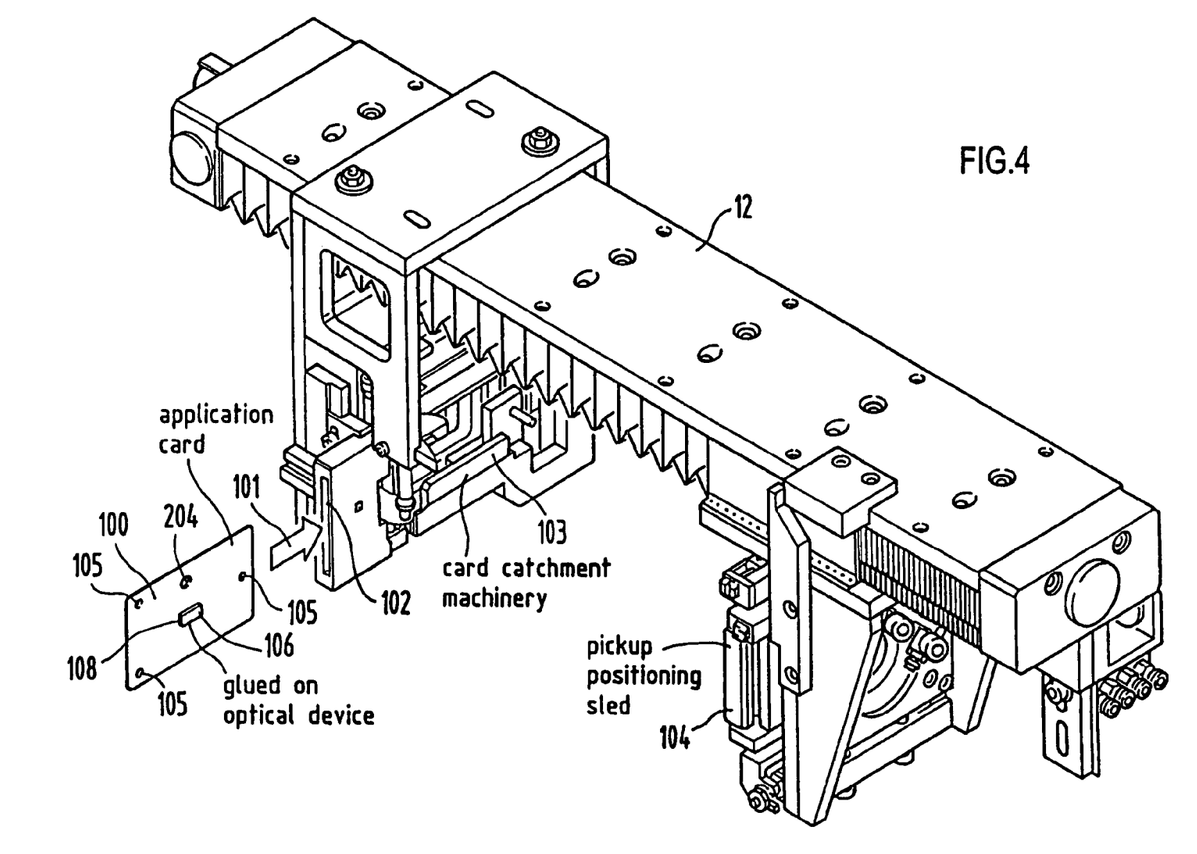
FIG. 4 is another view of the mechanism in FIG. 3.

Referring to FIG. 3, an aperture card system 12 is illustrated according to an embodiment of the invention. FIG. 4 shows another view of the aperture card system 12. After starting the laser system 10 and entering patient data in the computer 17, software of the system 10 requires the aperture card 100 to be inserted into the system 12. Arrow 101 shows the direction in which the card 100 is inserted into the system 12, preferably from a sleeve or holder (not shown) that protects the aperture card 100 and keeps it clean. The aperture card 100 is fed in a first orientation, for example, laterally, to card catchment or receiving machinery 103 (e.g., a lateral loading mechanism) by hand through a slot 102, although, in other embodiments, this can be automated. The card catchment machinery 103 pulls the aperture card 100 inside the laser system 10. A pickup-and positioning sled 104 (e.g., a vertical loading mechanism) moves forward to the card catchment machinery 103, as generally indicated by arrow 101' in FIG. 3, which transfers the aperture card 100 over to the pickup-and positioning sled 104. The pickup-and positioning sled 104 moves backwards, generally indicated by arrow 101" in FIG. 3, to a desired diaphragm position, and loads the aperture card 100 in a second orientation, for example, vertically, for accurate positioning and locking (e.g., in a vertical position) in the optical path of the excimer laser 15 by pins, as described below. Then, the pickup-and positioning sled 104 extracts itself to a place away from the secured card 100 and out of the way of the laser shots. The laser treatment procedure of the eye then can be started.

Also shown in FIGS. 3 and 4 are three positioning holes 105, which are used to position the card 100 on pins within the laser system 10, as will be described below. Near the middle of the card 100 is an aperture mounting slot 106 to hold an aperture mask 108. The mask 108 is mounted into the slot 106 of the aperture card 100, preferably being glued in place.

Figure 5:
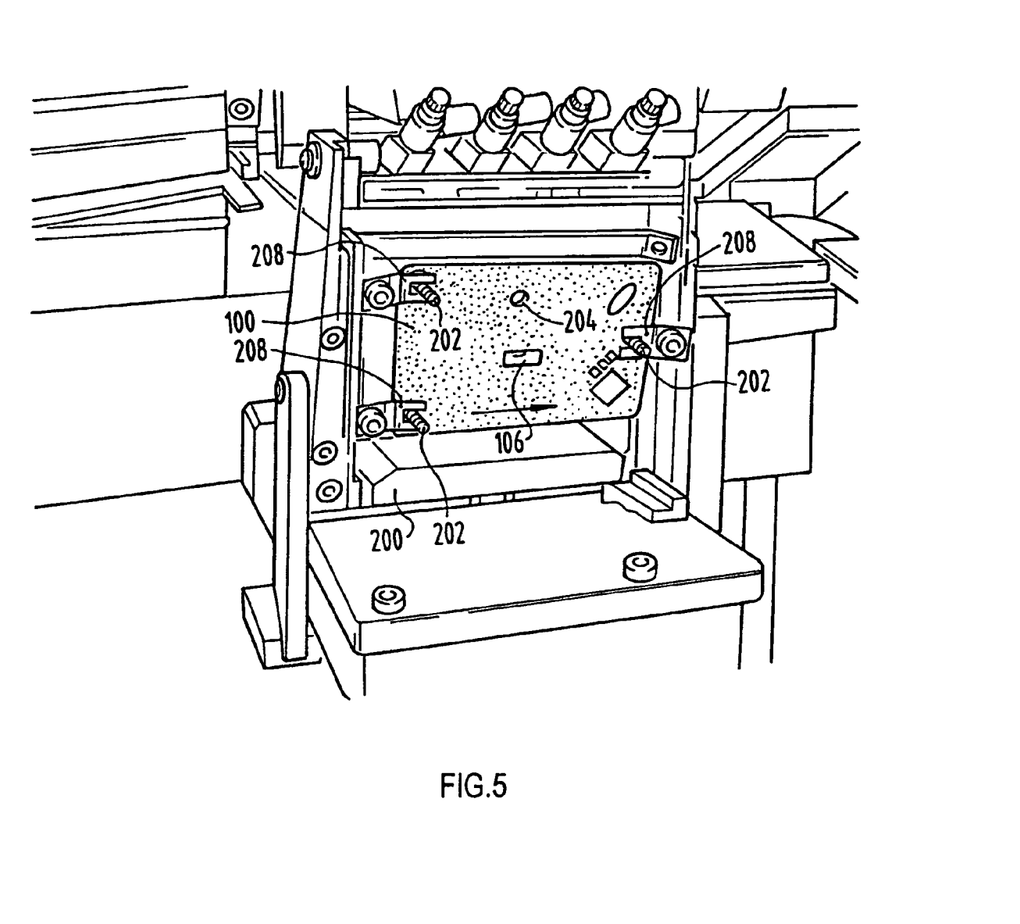
FIG. 5 illustrates a view of a portion of the mechanism of FIG. 3, including the aperture card of FIG. 2 in accordance with an embodiment of the invention.
Figure 6:
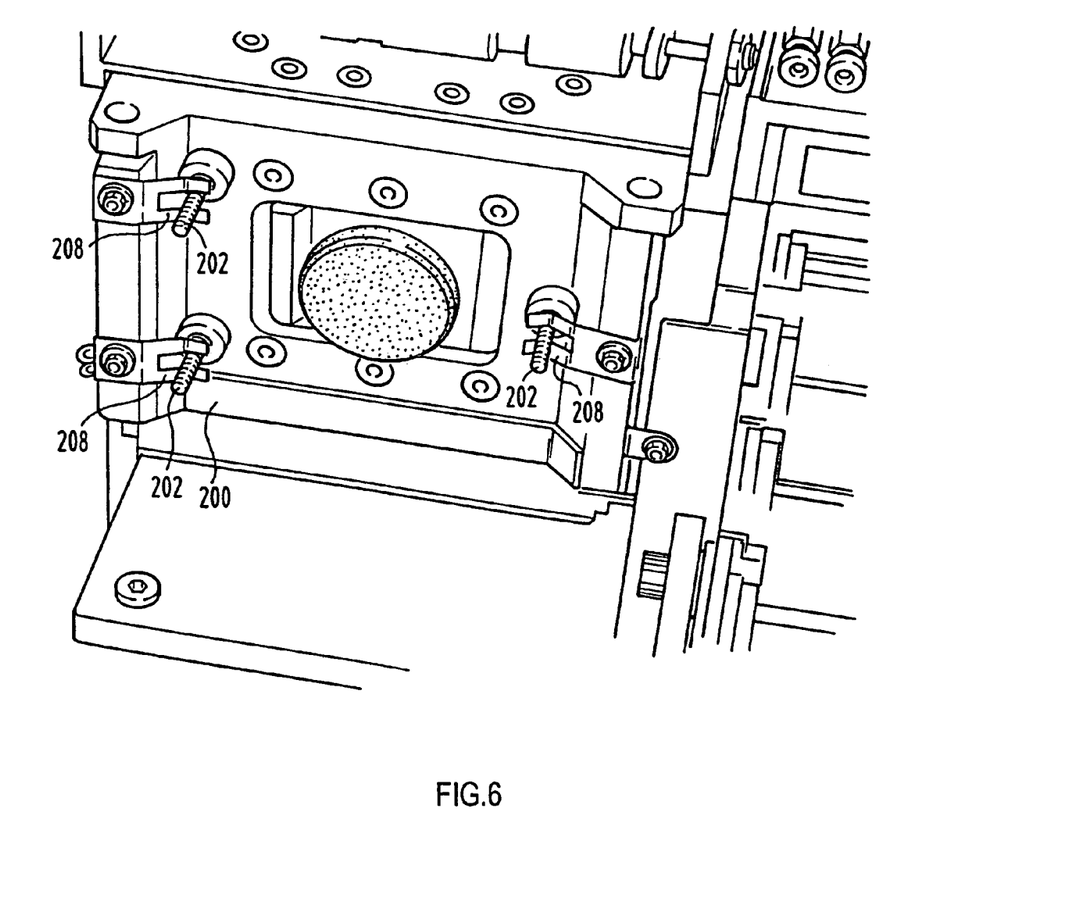
FIG. 6 illustrates another view of the portion of FIG. 5 with the aperture card of FIG. 2 removed.

Referring to FIG. 5, according to an embodiment of the invention, the aperture card 100 is illustrated positioned, after transfer, in an aperture card holder 200 of the laser system 10. As can be seen, three pins 202 pass through the pin holes 105 (see also FIG. 3) for precise positioning of the aperture card 100 (one pin 202 is obscured from view in FIG. 3 and all are obscured in FIG. 4). Further, in some embodiments, an alignment hole 204, shown in FIGS. 3–5, is provided for reference by lasers alignment within the excimer laser system 10 to align the aperture card 100 within the system before the aperture card 100 is employed. The laser system determines whether the aperture card 100 is properly positioned, inhibiting lasing action if the card is not positioned within tolerance. Alternatively, the laser system 10 can determine the position and adjust the computed ablation profile or otherwise adjust the optical system to adapt for the misalignment of the aperture within the aperture card. FIG. 6 illustrates the pins 202 in more detail along with clips 208 used to hold the aperture card 100 (not shown in FIG. 5) in place in the aperture card holder 200. It will be apparent to those skilled in the art that variations on this embodiment could be used to mount the aperture card 100 in position, including, for example, a different number of pins like the pins 202 and a different number of holes in the card 100 like the holes 104.

Figures 7, 7A, 7B, 7C, 7D, 7E, 7F, 7G, 7H:
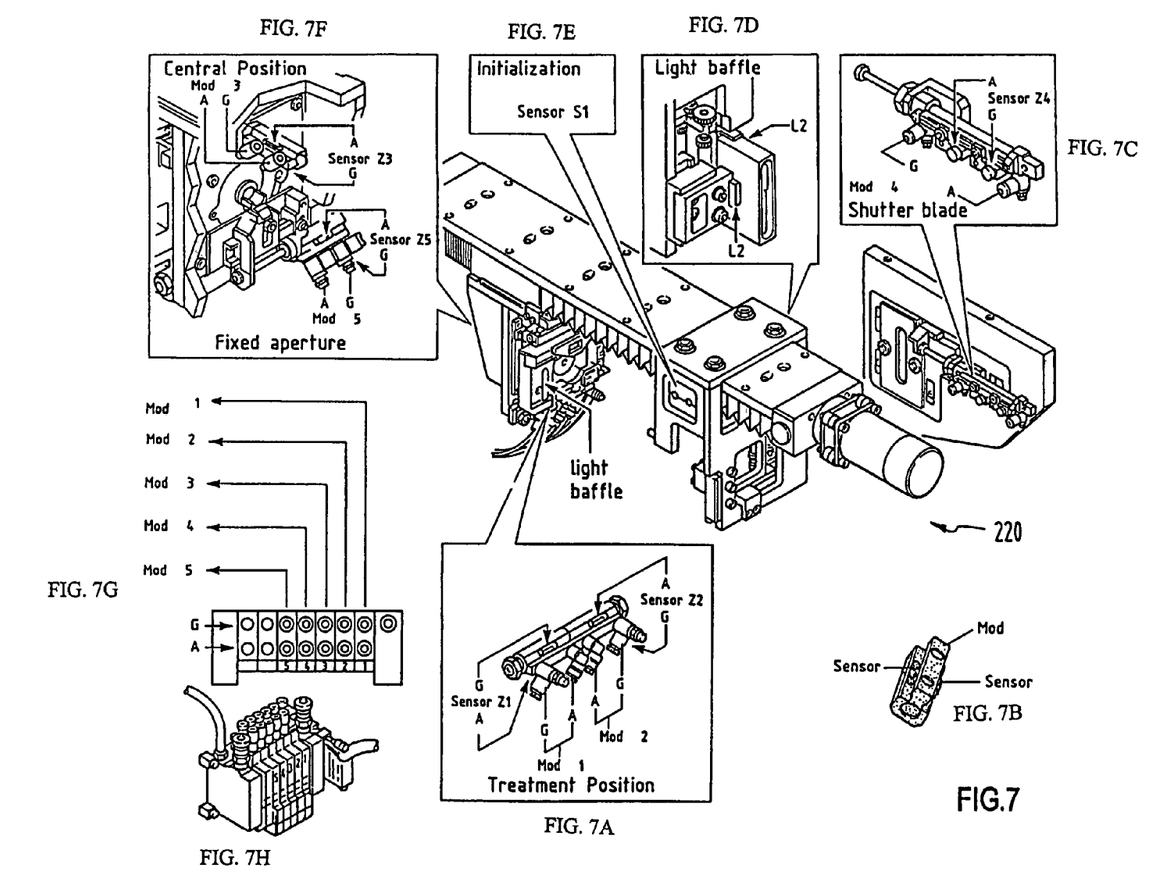
FIG. 7 illustrates a mechanism for holding an aperture card in place according to another embodiment of the invention.
Figure 8:
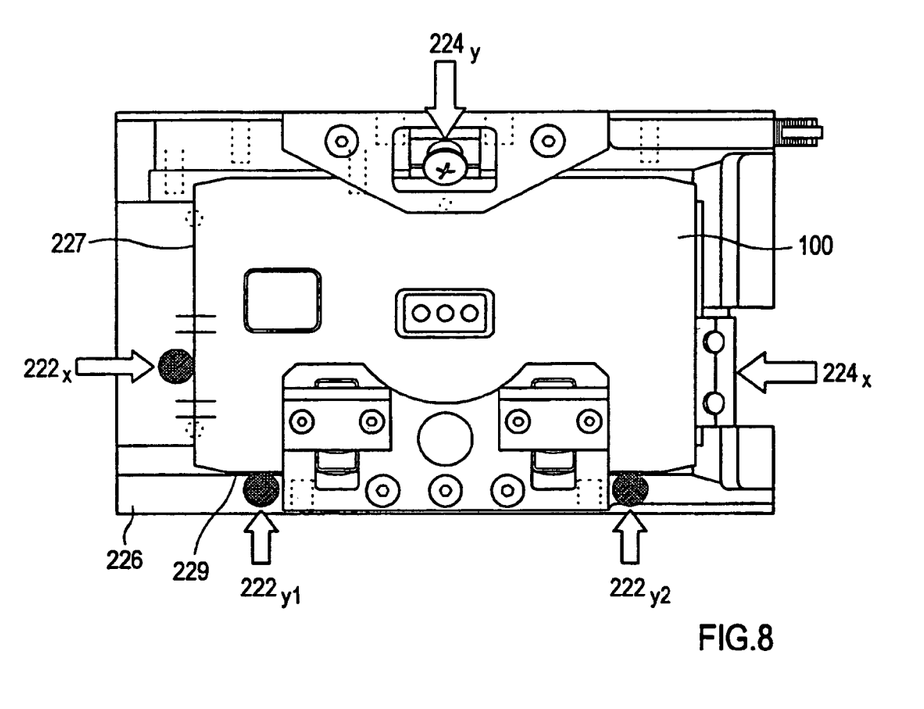
FIG. 8 illustrates an alternative position and alignment mechanism for the aperture card corresponding to FIG. 7.

In an alternative aspect of this embodiment, illustrated with reference to FIGS. 6 and 7, a pressure based mechanism is used in place of alignment holes and positioning pins to position, align and secure the aperture card 100. FIG. 7 shows a preferred aperture card system 220 having a common structure, in part, with the aperture card system 12 in FIGS. 3 and 4. The primary distinction resides in the replacement of the alignment pins 202 (FIG. 5) and corresponding alignment holes 105 in the aperture card 100 with fixation points 222 and pressure points $224_x$, $224_y$, as shown in FIG. 8. In an aspect of this embodiment, the fixation points 222 comprise three hardened cylinder pins that are press fit into the card holder 26 with high accuracy. The card 100 is pushed into the holder 226 from right to left (as viewed in FIG. 8) until the left edge 227 of the card touches fixation point $222_x$ and the bottom edge 229 of the card touches fixation points $222_{y1}$, and $222_{y2}$. The card is fixated against the fixation points by pressure points $224_x$, $224_y$ which, preferably, are springs. By manufacturing the card 100 with high precision such that the exact location of the apertures are known, and the fixation points engage the card edges at the same locations, repeated positioning of the cards has shown a measured accuracy of ±5 µm or better.

The mask 108 is preferably constructed of an opaque coating (e.g., chromium deposited or otherwise coated or layered) on quartz. More preferably, the coating is a multi-layer coating including a layer of titanium overlaying the chromium layer, and a layer of gold overlaying the titanium layer. Most preferably, the multilayer coating consists of a chromium layer approximately 80 nm thick adjacent the substrate, a titanium layer approximately 40 nm thick adjacent the chromium layer, and a gold layer approximately 80 nm. thick adjacent the titanium layer. The aforementioned layered coating advantageously reduces unwanted reflection of laser light. The mask includes a 2 mm effective diameter (or substantially 2 mm effective diameter) "soft spot" (defined in more detail below) aperture, a similar 1 mm (or substantially 1 mm effective diameter) soft spot aperture, and a center, 2 mm effective diameter (or substantially 2 mm) "hard" aperture having a square edge. Unlike the mask in the aforementioned U.S. Pat. No. 5,376,086, patterning of the mask 108 is independent of eye topography data and can be used for any eye topographical surface, including any corneal surface. Depending upon the optical system employed by the excimer laser system 10, the actual overall diameter of the apertures referred to above may be larger or smaller than the corresponding image or irradiance pattern projected onto an eye. For example, typical illustratively useful 2 mm diameter and 1 mm diameter spots on the eye can correspond to 3 mm and 1.5 mm overall diameter aperture patterns, respectively.

The "hard" square edge aperture is used for fluence testing with a standard fluence plate, such as a polyethylene foil coated on both sides with aluminum. It is preferable to perform the fluence test with a square edge aperture for system calibration because it is easier to see how many shots are required to ablate through material from one layer to the next or to penetrate to a particular depth using a square edge profile beam than it is with the rounded profile ablation of a non-square edge aperture.

Figure 9:
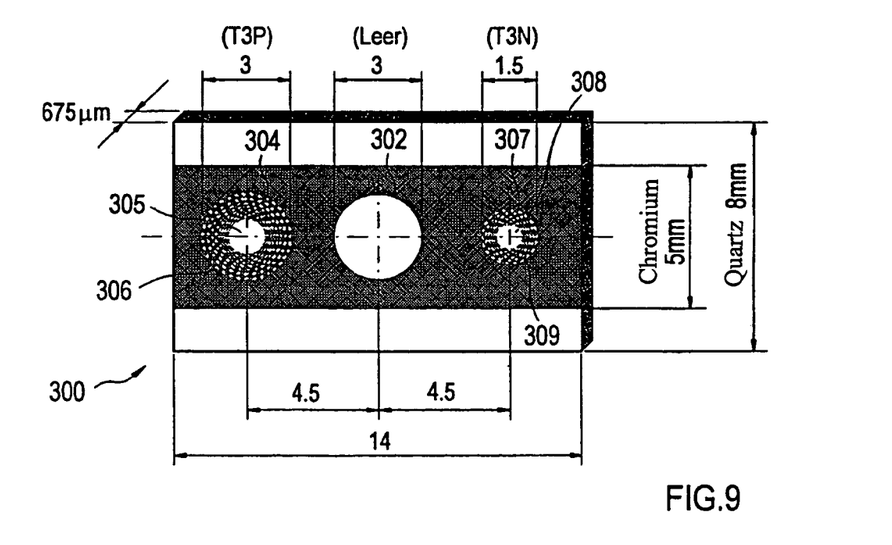
FIG. 9 is a mechanical drawing illustrating an aperture mask that forms a portion of an aperture card in accordance with an embodiment of the invention.
Figure 10:
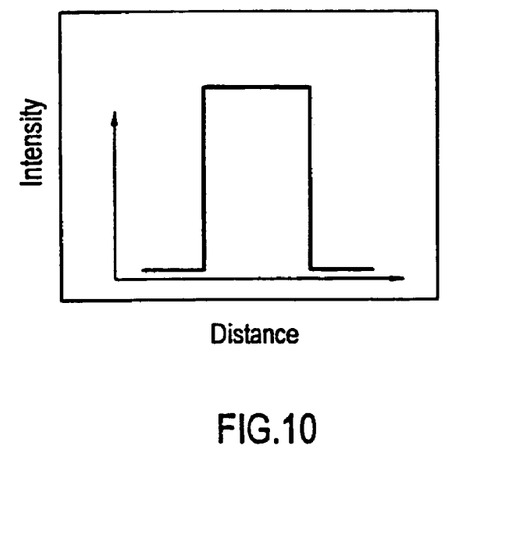
FIG. 10 illustrates a square-sided spatial intensity profile of an aperture having a square edge that forms part of the aperture mask of FIG. 7 in accordance with an embodiment of the invention.

Referring to FIG. 9, a mechanical drawing is illustrated of an aperture mask 300, which is exemplary of the aperture mask 108 that can fit into the aperture slot 106, and preferably glued into place. As shown in FIG. 9, a "hard"-edged, center aperture 302 has an overall diameter of 3 mm or substantially 3 mm that simply passes a standard square-sided (i.e., square-profiled) laser shot, such as that shown in FIG. 10. A 3 mm overall diameter soft spot aperture 304 includes a center aperture area 305 surrounded by a pattern of microscopically small holes 306 that, through direct diffractive effects, create the appropriate ablation profile. Finally, a third soft spot aperture 307 is 1.5 mm or substantially 1.5 mm in overall diameter, which also includes a center aperture area 308 and small microscopic holes 309 similar to those of the aperture 304 to create the appropriate ablation profile, an exemplary embodiment of which is discussed below in connection with FIG. 11. Although FIG. 9 illustrates the aperture mask 300 having a single 3 mm diameter hard edged aperture, a 3 mm diameter soft spot aperture, and a 1.5 mm diameter soft spot aperture, it is contemplated that more or less of these numbers and types, and possibly different diameters, of these apertures could be included in the aperture mask 300, all of which are included within the scope and spirit of the present invention. As discussed above, these apertures typically are projected onto the eye either reduced or enlarged; here, the 3 mm diameter and 1.5 mm diameter apertures preferably create 2 mm diameter and 1 mm diameter spots on the eye.

Prior to performing an ablation, the card holder 200 moves (e.g., laterally), according to the desired excimer laser system, to employ a fluence test (in which case the 3 mm center square profile aperture 302 is placed into position) and then for the laser ablations of the eye, either the soft spot aperture 304 (e.g., 2 mm imaged spot or 307 (e.g., 1 mm imaged spot is placed into position. The soft spot apertures are employed in laser ablating by laterally moving the aperture card 100 (e.g., left and right) within the aperture card holder 200.

Again, the soft spot apertures 304 and 307 of FIG. 9 are focused by the system 10, preferably down to 2 mm and 1 mm or substantially those values, respectively. Again, the apertures 302, 304, and 307 are preferably formed on a quartz plate 308, using a suitably deposited mask as described herein. The mask can then be appropriately etched using a laser etching system, as will be appreciated by those skilled in the art. Alternatively, photolithography, silicon wafer technology, chip card technology, or other techniques can be employed to create the mask 300.

Figure 11:
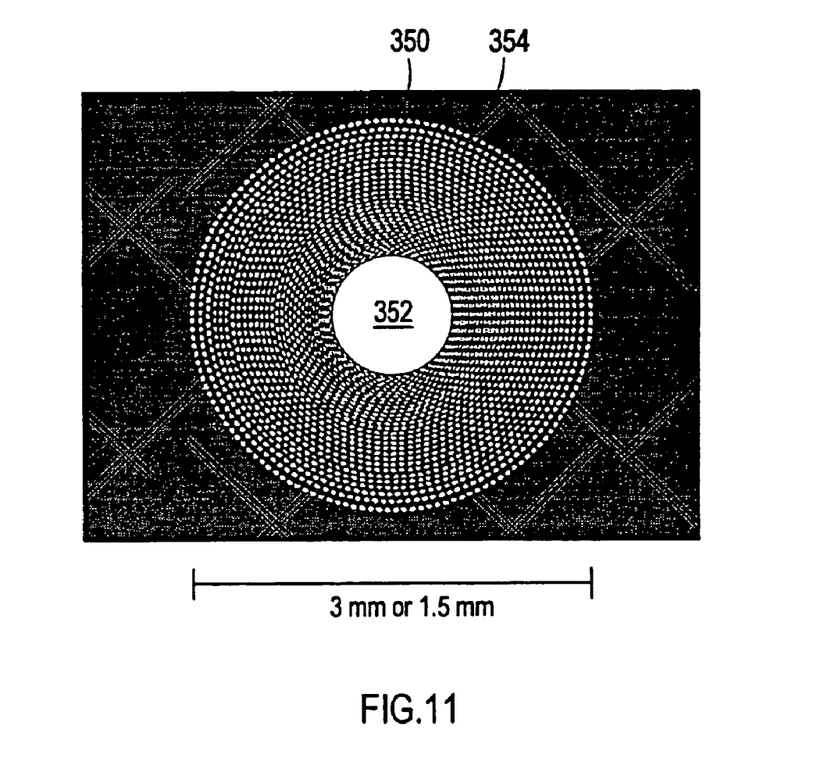
FIG. 11 illustrates a "soft" spot aperture in accordance with an embodiment of the invention.

FIG. 11 is a more detailed illustration of an exemplary soft spot aperture 350 that can be used for the soft spot apertures 304 or 307. The soft spot aperture 350 is shown having a central open aperture 352 like the apertures 305 and 308 of FIG. 9, surrounded by microscopic holes 354 like the holes 306 and 309. Once the spatial intensity profile is specified, a variety of known techniques can be employed to design and position the holes, and knowledgeable artisans would be able to create such an aperture. By providing a spatial intensity profile, a soft spot aperture that would produce such a profile (e.g., like that of FIG. 11) can be obtained from Fraunhofer Institut Siliziumtechnologie, Faunhoferstraβe 1, D-25524 Itzehoe, Germany, and from others.

Figure 12:
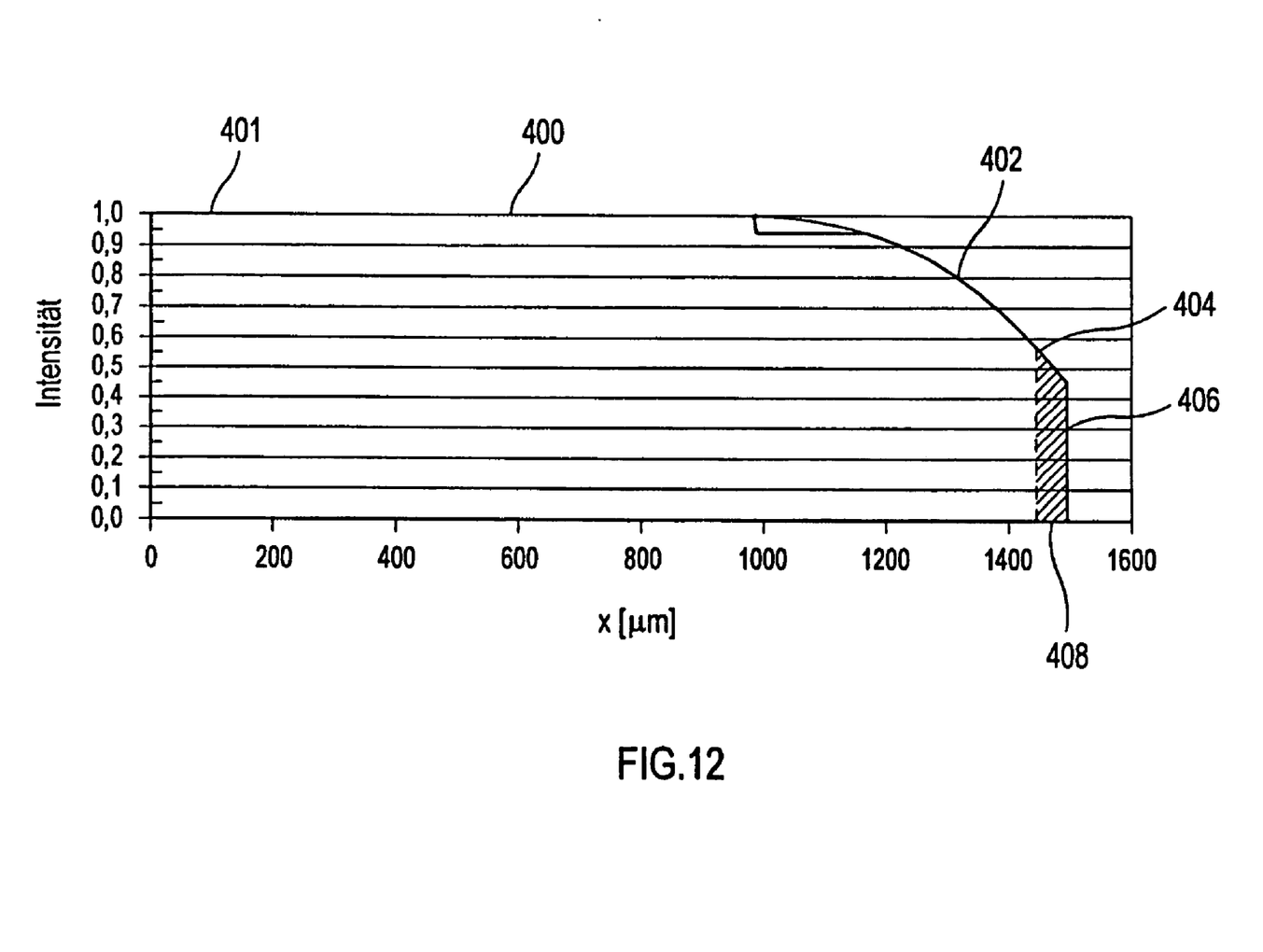
FIG. 12 illustrates a useful ablation profile passed by a soft spot aperture in accordance with an embodiment of the invention.

Referring to FIG. 12, a useful ablation profile (or spatial intensity distribution) 400 passed by the soft spot aperture 304 is shown in accordance with an embodiment of the invention. In FIG. 12, the profile is normalized and only one-half the profile 400 is illustrated, solely for simplicity of the drawing, it being understood that the full profile 400 would be as if mirrored about the ordinate axis of FIG. 12. The aperture 307 would pass a similar, but narrower, profile. As can be seen, a center portion 401 of the aperture profile 400 is flat or substantially flat, whereas an edge 402 of the profile 400, continuous with the portion 401, is rounded. The portion 401 is preferably symmetric about the radius of the profile and extends across about 60–80%, and, more preferably, across about 65–70% of the profile 400. At a certain point, such as an intensity threshold point 404 at which the eye tissue ablation intensity threshold is no longer reached, the profile 400 preferably quickly drops off or diminishes as a substantially square, vertical, or truncated edge 406. The ablation threshold and any variations in it are known in the art. The amount of energy falling below the threshold for ablation is preferably about 5% or less of the total energy encompassed by the profile 400. The profile 400 is non-Gaussian, for example, between square and Gaussian-shaped, or a truncated Gaussian.

Thus, an automatic system is employed to position the aperture card 100 at the position in which the aperture mask 300 passes an ablation profile with a substantially flat or flattened top, rounded edges, and substantially truncated sides for ablation of corneal tissue. Further, the card 100 can be laterally moved into positions for laser shots at a larger "soft edged" spot size, a smaller "soft edged" spot size, or at a center portion suitable for adjusting fluence levels.

One advantage of the profile 400 of FIG. 12 is that, by having a "flat" top, a relatively uniform ablation is produced, which assists in steepening the sides of an ablation, although the resulting profile in tissue is more round than for a square profile. This, like for a Gaussian profile, is also advantageous in avoiding a "haze" that can result from square profile ablations. The goal in the design and use of the profile 400 is to maximize the ablation per shot while avoiding the haze encountered with square profile ablations. The width of the flat portion and the amount of energy below threshold, as discussed above, is driven by this goal. Also, the rounded and vertical edges reduce the "stair-step" effect of typical ablations with square-sided ablation profiles, which could affect healing. Further, by employing the profile 400, by appropriate mask 300 design, nearly all of the eye tissue can be removed that normally would be removed with a square-sided ablation profile passed, for example, by the aperture 302, but with rounded and vertical edges. Thus, the soft spot profile combines both the advantages of the Gaussian profile and the square profile.

Figure 13:
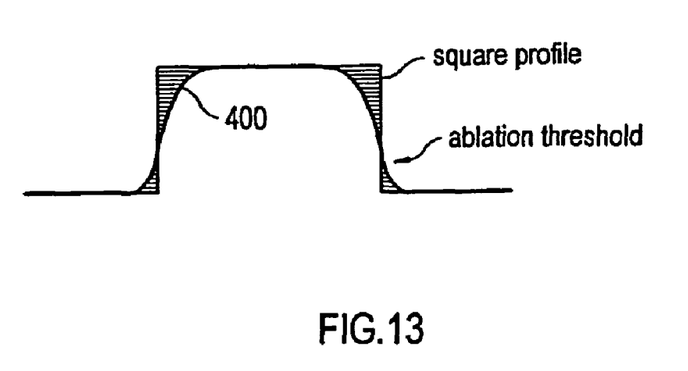
FIG. 13 illustrates a comparison between a square profile and a soft spot profile in accordance with an embodiment of the invention.

In FIG. 12, although there is a small portion 408 of the ablation profile 400 that might not reach the necessary ablation threshold, this portion is designed to be a very small fraction of the overall ablation profile 400. By contrast, typically for a Gaussian profile, a much larger amount of energy falls below the ablation threshold. When the ablation threshold is not reached, typically the tissue merely is heated, rather than ablated. Without ablation, the resulting heating diminishes one of the advantages of a 193 nm laser system. It is therefore desirable to reduce this effect because heating may effect a later ablation of the heated tissue or other nearby tissue, or may have other effects, such as producing scarring or opacities. The total energy below threshold of the profile 400 is preferably limited to reduce heating while maximizing ablation. By designing the portion 408 to be small, possible detrimental thermal heating below threshold is reduced or minimized. FIG. 13 illustrates a comparison of a square profile (e.g., if the aperture 302 or a similar aperture were used to ablate) with the soft aperture profile 400. Little of the total energy of the profile 400 appears outside the square profile, as indicated by the outside hatched area.

Figure 14A:
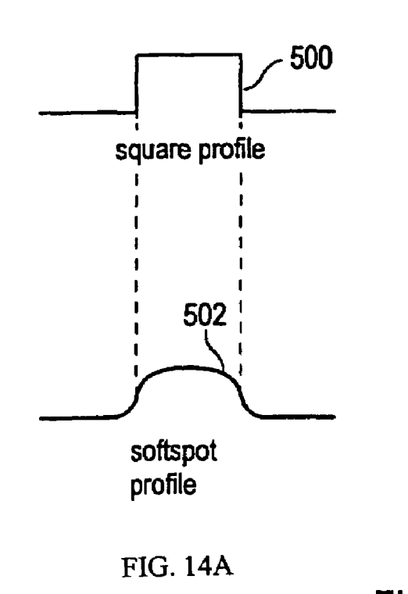
FIG. 14 illustrates a comparison between a square profile and a soft spot profile with their resulting tissue ablation profiles.
Figure 14B:
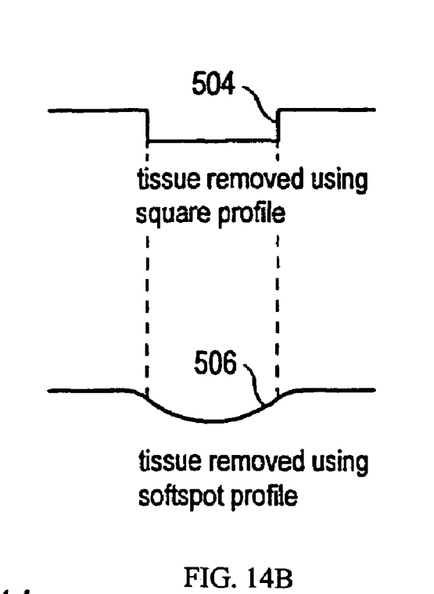

Compared to standard ablation profiles, the profile 400 of FIG. 12 has many advantages, including that it uniformly removes nearly all of the eye tissue normally removed by a square-sided ablation profile (e.g., typically within 90%, although other designs, such as 80%, are possible), but its edges are still "rounded," thereby rounding the tissue removed on each laser shot. FIG. 14 illustrates a comparison between a square profile 500 with a resulting laser shot ablation profile 504 in eye tissue and a profile 502 like the profile 400, according to the invention, with its rounded laser shot ablation profile 506 in eye tissue. By rounding the edges of the tissue removed in each shot, advantages also include allowing iris tracking systems to more continuously and accurately track the location of the pupil. This is because using square-sided shot profiles, the "haze" discussed above can appear on the eye before a LASIK flap is returned into position that can interfere with the ability of the eye tracker to track the pupil position on the eye. Further, there are fewer healing effects and the eye can more quickly return to a natural sight condition when the edges are rounded.

It is possible that the aperture mask 300 of FIG. 9 (or the aperture mask 108, or even the aperture card 100, of FIG. 4) may wear out more quickly than a typical diaphragm card using an excimer laser system. This is for a variety of reasons, including the possibility that the quartz employed for the aperture mask 300 will become slightly more opaque over time. Because chromium-on-quartz is the preferred manufacturing technique, it is desirable thus to replace the aperture card with each excimer treatment for a new patient in the interest of surgical precautionary considerations and to achieve the highest quality ablations, in addition to reproducibility. The card can, for example, be treated with a laser blast or provided with an electronic signature that disables the card from further use.

Further, the aperture card 100 can also incorporate electronic circuitry to provide the laser system 10 information and validation of procedures to be performed. For example, the aperture card 100 can include an SLE 4428 secure chip memory. This typically is encoded with a variety of data, such as the serial number of the machine (or machines, such as for a laser center) on which the card 100 is validated for use, the number of procedures available with the particular card 100, what types of treatments are permitted, and perhaps storage of a control number and patient name after the treatment is performed for tracking purposes. With sufficient storage, the actual treatment profiles or iris alignment and verification data could also be included. Preferably, the electronics prevent use of the excimer laser system without appropriate validation, such as through a PIN number, and prevent extra uses of the card 100.

A variety of techniques can be employed to create ablation profiles using these soft spot apertures for custom refractive correction in which the laser system determines the shot pattern necessary to achieve the ablation profile. In a preferred embodiment, laser beams having the soft spot intensity profile of this invention are used in a dual-mode, laser surgery system for the eye. In the dual mode system, the eye is first treated ("shaped") for primary corneal defects, such as myopia, hyperopia, and astigmatism, using a larger, fixed spot size. Then, a smaller fixed spot size is used to remove remaining irregularities ("polished"). The larger size spot provides faster treatment. The smaller size spot provides more precision in the treatment of irregular topographies. The size of the larger spot is desirably a relatively large fraction of the typical area of the cornea to be subject to ablation. The larger spot is typically between about 2 and 3.5 mm, preferably about 2 mm in diameter. The smaller spot is typically not larger than about 1 mm in diameter, and is preferably about 1 mm in diameter. For example, in U.S. patent application Ser. No. 09/591,313 and International Patent Publication WO 98/48746 (PCT application No. PCT/EP98/02428), a dual spot size system is described that employs 1 mm and 2 mm square profile spot sizes that are scanned over a corneal surface to create a desired ablation profile. As a particular, non-limiting example, the 2 mm soft spot aperture can be used to treat 80% of a desired ablation in a lower resolution first pass and the remaining 20% treated with the 1 mm soft spot aperture in a higher resolution second pass. Other relative percentages are possible.

Using the scanning ("Plano-scan") techniques described in U.S. Pat. No. 6,090,100 (U.S. patent application Ser. No. 08/324,782; PCT application No. PCT/EP95/04028, and in International Patent Publication WO 94/07447 (PCT application PCT/EP93/02667), the soft aperture spots of the present invention, in another embodiment, can be employed to create any desired ablation profile, and particularly, customized ablation profiles for irregular ablations other than simple myopic, hyperopic, and astigmatic profiles. Moreover, the soft spot apertures of the present invention, in another embodiment, can be employed to create spiral shot patterns and randomized shot patterns using the techniques described in International Patent Publication WO 94/11655 (PCT application PCT/EP95/04028). These techniques can include ablations made with a single, fixed spot size.

Eye topography systems, such as the ORBSCAN and ORBSCAN II® by Bausch & Lomb/Orbtek®, Inc., Salt Lake City, Utah, are known in the art. Eye topography data, preferably elevation-based eye topography data, including corneal topography data, as well as wavefront sensor data, for example, as disclosed in U.S. Pat. No. 5,777,719, issued to Williams et al., can be used by an eye surgeon or automated for identifying regions of the cornea requiring ablations for vision correction. Such techniques are known to those skilled in the art. These data can be transformed for use in conjunction with the soft spot apertures and the aperture card of the present invention for making ablations in performing customized refractive correction surgery.

The foregoing disclosure and description of the preferred embodiment are illustrative and explanatory thereof, and various changes in the components, circuit elements, circuit configurations, and signal connections, as well as in the details of the illustrated circuitry and construction and method of operation may be made without departing from the spirit and scope of the invention.

The invention claimed is:

1. An aperture card for use in a photorefractive laser system, for producing a desired laser beam profile at a target, wherein the card has a soft spot aperture pattern, comprising a transparent substrate, said substrate having a coating; and means for positioning the card in the laser system.

2. The aperture card of claim 1 wherein said coating is adapted to provide only a single use of the card.

3. The aperture card of claim 1 further comprising a hard aperture.

4. The aperture card of claim 1 wherein said positioning means comprises a positioning hole.

5. The aperture card of claim 1 further comprising an electronic disablement device.

6. The aperture card of claim 1 wherein the desired beam profile has a substantially flat top portion, a rounded edge section and a straight, vertical side portion.

7. The aperture card of claim 6 wherein the flat top portion and a substantial portion of the edge section are above an ablation threshold value for corneal tissue.

8. The aperture card of claim 1 wherein said coating is a layered structure comprising chromium, titanium and gold.

9. The aperture card of claim 8 wherein said chromium layer is adjacent said substrate, said titanium layer is adjacent said chromium layer, and said gold layer is adjacent said titanium layer.

10. The aperture card of claim 9 wherein said chromium layer and said gold layer are approximately 80 nm thick and said titanium layer is approximately 40 nm thick.

11. The aperture card of claim 1, said card having at least two soft spot aperture patterns, each of the aperture patterns having a different effective size for producing, respectively, different fixed size beam profiles at the target.

12. The aperture card of claim 11 wherein each soft spot aperture pattern comprises a larger central aperture and a plurality of smaller apertures for providing the effective size of each aperture pattern.

13. The aperture card of claim 11 wherein one of the at least two soft spot aperture patterns has an effective diameter of approximately 3 mm and another of the at least two soft spot aperture patterns has an effective diameter of approximately 1.5 mm.

14. The aperture card of claim 13 wherein the one of the soft spot aperture patterns is adapted to create a first beam spot having the desired beam profile at the target, said first beam spot having a diameter at the target of approximately 2 mm, and the another of the at least two soft spot aperture patterns is adapted to create a second beam spot having the desired beam profile at the target, said second beam spot having a diameter at the target of approximately 1 mm.

15. The aperture card of claim 11 further comprising a hard aperture.

16. The aperture card of claim 15 wherein said hard aperture provides a top hat beam profile at the target.

17. A laser system, comprising:
an excimer laser source providing light for volumetric removal of tissue for refractive correction of an eye;
an optical system propagating at least a portion of the light; and
an aperture card holder, positioned for holding a removable aperture card having at least one soft-spot aperture pattern, positioned within a path of the light, wherein the aperture card is laterally moveable into at least a first position for the passage of light through the at least one soft-spot aperture patterns for laser ablation of the eye and into at least a second position for the passage of light through another aperture for testing the fluence of the laser system.

18. The system of claim 17, further comprising:
a control system coupled to the aperture card holder, the laser source, and the optical system, and controlling them to provide a vision correcting ablation profile.

19. The system of claim 17, further comprising at least one alignment laser positioned to verify alignment of the aperture card in the aperture card holder prior to volumetric removal of the tissue.

20. The system of claim 17, wherein the aperture card comprises a plurality of aperture patterns, and wherein the aperture card holder is adapted to place one of the plurality of aperture patterns in the path of the light.

21. The system of claim 17, further comprising:
a card conveyance system adapted to receive the removable aperture card and to convey the aperture card into an appropriate position in the aperture card holder.

22. The system of claim 21, wherein the card conveyance system further comprises:
a receiving slot for receiving the aperture card;
a first orientation loading mechanism arranged to extract the aperture card via a receiving mechanism and transport it to a vertical loading mechanism;
a second orientation loading mechanism arranged to receive the aperture card from the vertical loading mechanism and to load the aperture card into the aperture card holder.

23. The system of claim 17, wherein the aperture card holder further comprises a plurality of pins adapted to align the aperture card when the aperture card is placed into position in the aperture card holder.

24. The system of claim 11, wherein the aperture card holder has three vertical pins.

25. The system of claim 17, wherein the aperture card is moveable into a third position for the passage of light through another soft-spot aperture patterns for ablation of the eye tissue.

26. The system of claim 25, wherein the at least one and the another one of the soft-spot apertures patterns, respectively, pass a beam of substantially a first fixed size and a second fixed size having a desired ablation profile.

27. The system of claim 17, wherein the aperture card holder further comprises a fixation point and a pressure point, wherein said pressure point provides a pressure for engaging said aperture card with the fixation point.

28. The system of claim 27, wherein the pressure point is a spring and the fixation point provides a mechanical stop.

29. A method for providing a laser beam suitable for performing laser ablation of an eye, the method comprising: providing the laser beam onto the eye conditioned to have a profile with a substantially flat top and substantially rounded sides that are substantially vertical below an ablation threshold value.

30. A method for providing a laser beam suitable for performing laser ablation of an eye, the method comprising:
generating a laser beam;
positioning an aperture card having an aperture pattern in the path of the laser beam such that said beam intercepts said aperture pattern;
providing a spatial intensity distribution of the laser light at a desired location on the eye using the aperture card, wherein said spatial intensity distribution includes a substantially flat top portion, a rounded edge portion continuous with the top portion, and a substantially vertical portion continuous with the edge portion.

31. The method of claim 30, further comprising using topography data in conjunction with the spatial intensity distribution for ablating the eye for vision correction.

32. The method of claim 30, wherein the topography data is elevation-based.

33. The method of claim 30, further comprising using wavefront sensor data in conjunction with the spatial intensity distribution for ablating the eye for vision correction.

34. The method of claim 30, wherein the forming the spatial intensity distribution comprises positioning the substantially vertical portion below an ablation threshold intensity position of the spatial intensity profile.

35. The method of claim 30 wherein said aperture pattern is a soft spot aperture pattern.

36. The method of claim 35 wherein providing the spatial intensity distribution comprises forming a laser spot having an effective diameter of between about 2 mm–3.5 mm, or, less than or approximately equal to 1 mm.

37. The method of claim 36 wherein the effective diameter is approximately 2 mm, or, approximately 1 mm.

38. The method of claim 30 wherein said aperture card comprises at least two aperture patterns having different effective diameters, further comprising:
   ablating eye tissue with a first series of laser shots having the spatial intensity distribution;
   positioning the different diameter aperture in the path of the laser beam to form a second spatial intensity distribution similar to the spatial intensity distribution and having a different effective size of the spatial intensity distribution; and
   ablating eye tissue with a second series of laser shots having the second spatial intensity distribution.

39. The method of claim 38, wherein the spatial intensity distribution has an effective diameter at the eye of between about 2 mm–3.5 mm and the second spatial intensity distribution has an effective diameter at the eye of less than or approximately equal to 1 mm.

40. The method of claim 39 wherein the spatial intensity distribution has an effective diameter of approximately 2 mm and the second spatial intensity distribution has an effective diameter of approximately 1 mm.

41. The method of claim 30, wherein said aperture card comprises a different aperture pattern for forming a spatial intensity distribution suitable for measuring a fluence of the laser beam, further comprising positioning said different aperture pattern in the path of the laser beam; and measuring the fluence of the laser beam.

42. The method of claim 41, wherein said different aperture pattern is a hard aperture.

43. The method of claim 41, wherein said spatial intensity distribution from said different aperture pattern has substantially a top-hat profile.

* * * * *